US00PP22078P3

(12) United States Plant Patent
Bacon et al.

(10) Patent No.: US PP22,078 P3
(45) Date of Patent: Aug. 16, 2011

(54) GRAPEVINE PLANT NAMED 'SUGRATHIRTYSIX'

(50) Latin Name: *Vitis vinifera*
Varietal Denomination: Sugrathirtysix

(75) Inventors: Terry Bacon, Bakersfield, CA (US); Michael Striem, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 12/592,053

(22) Filed: Nov. 18, 2009

(65) Prior Publication Data

US 2011/0119798 P1 May 19, 2011

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

PP14,088 P3 8/2003 Cain

*Primary Examiner* — June Hwu
(74) *Attorney, Agent, or Firm* — Knobbe, Martens, Olson & Bear, LLP

(57) ABSTRACT

A new and distinct grapevine variety characterized by producing early ripening, round berries with uniform red colored berry skin. The berries have high sugar content and a mild, sweet Muscat flavor. A cluster of fruit has good attachment, but is not as compact as those of other comparable varieties.

1 Drawing Sheet

Latin name of the genus and species claimed: *Vitis vinifera*. Variety denomination: 'SUGRATHIRTYSIX'.

BACKGROUND AND SUMMARY OF THE INVENTION

This invention relates to the discovery and asexual propagation of a new and distinct variety of grapevine as herein described and illustrated. The new variety was first hybridized by Michael Striem and Terry Bacon in Wasco, Kern County, Calif., the variety being originated by controlled hybridization.

The new variety 'Sugrathirtysix' is characterized by producing early ripening, round berries with uniform red colored berry skin. The berries of 'Sugrathirtysix' have high sugar content and a mild, sweet Muscat flavor. A cluster of 'Sugrathirtysix' fruit has good attachment, but is not as compact as those of other comparable varieties.

The seed parent is the varietal selection '97001-198-219' (unpatented) and the pollen parent is the varietal selection '93018-070-024' (unpatented). The parent varieties were first crossed in May 2001 by Michael Striem and Terry Bacon. The date of first sowing was July 2002, and the date of first flowering was May 2004.

The new variety 'Sugrathirtysix' was first asexually propagated in December 2005, in Wasco, Kern County, Cailf., by Michael Striem using hardwood cuttings.

The new variety 'Sugrathirtysix' resembles its seed parent '97001-198-219' (unpatented) in many characteristics, such as the same mild Muscat flavor and early ripening time, but differs from its seed parent in that it has red rather than black, larger, more uniform berries. Additionally, 'Sugrathirtysix' is similarly productive, but the cluster structure is somewhat larger and longer with wider shoulders.

The new variety 'Sugrathirtysix' resembles its pollen parent '93018-070-024' (unpatented) in many characteristics, such as the same firmness. Additionally, similar to its pollen parent, 'Sugrathirtysix' has a good attachment of the berries. Unlike its pollen parent, the skin of the fruit is thinner and bite not as crunchy, but rather juicy. 'Sugrathirtysix' has a more uniform berry shape than its pollen parent with a mild Muscat flavor. The new variety also differs from its pollen parent in that the berries of the pollen parent are much smaller (approximately 2.3 gr.) whereas those of the new variety 'Sugrathirtysix' are larger (approximately 3.4 gr.). Additionally, 'Sugrathirtysix' ripens approximately two weeks before the pollen parent.

The new variety 'Sugrathirtysix' ripens early in the season, about seven to ten days before 'Flame Seedless' (a standard public non-patented variety) and about two months before 'Sugranineteen' (U.S. Plant Pat. No. 14,088).

The new variety 'Sugrathirtysix' resembles the comparable variety U.S. Plant Pat. No. 14,088, otherwise known as 'Sugranineteen', in its red color and sweet flavor. However, 'Sugrathirtysix' develops a mild muscat flavor unlike 'Sugranineteen'. The berries of 'Sugrathirtysix' are naturally smaller (approximately 3.4 gr. vs. approximately 5.6 gr.) and ripen about two months earlier. Clusters of 'Sugrathirtysix' are much smaller, and not as compact as those of 'Sugranineteen' (approximately 281 gr. vs. over 1000 gr. respectively).

The new variety 'Sugrathirtysix' differs from the variety 'Thompson Seedless' (unpatented) in that 'Sugrathirtysix' has a uniform red color, is more productive, has a larger natural berry size (approximately 3.6 gr. vs. approximately 2.5 gr. of the natural performance) and ripens about six weeks earlier. In addition, the berries of 'Sugrathirtysix' are firmer and have better attachment to the cluster's stem.

The new 'Sugrathirtysix' variety has been shown to maintain its distinguishing characteristics through successive asexual propagations by, for example, cuttings.

Variations of the usual magnitude from the described above may occur with changes in growing conditions, irrigation, fertilization, pruning, management and climatic variations.

BRIEF DESCRIPTION OF THE DRAWINGS

The accompanying drawing illustrates in full color a four year old plant with typical cluster of berries, a young shoot, and a mature leaf blade of the new grapevine. The colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England (2001).

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrathirtysix' plants grown in the vicinity of Wasco, Kern County, Cailf., during 2007 and 2008, and is believed to apply to plants of the variety grown under similar conditions of soil and climate elsewhere.

VINE

General: (Measurements taken on 4 year old vine unless otherwise noted.)

- *Planting.*—Trained to a modified gable trellis, planted in about 7 ft.×12 ft. spacing.
- *Practices.*—Gene-pool-vine: Cane pruned to approximately 2 canes per vine, 16-18 spurs per vine. Test-vines: Cane pruned to approximately 30 to approximately 40 spurs per vine, and tested also as cane pruned to approximately 2 canes per vine.
- *Size.*—Medium. Height: Approximately 2.0 m. Width: Approximately 2.2 m.
- *Vigor.*—Medium.
- *Fresh pruning weight.*—Approximately 6 kg per vine.
- *Density of foliage.*—Medium.
- *Productivity.*—Very productive — approximately 100 clusters per vine.
- *Yield.*—Approximately 12 kg per vine.
- *Crop load.*—Approximately 2 kg per vine (kg fruit per kg fresh-pruning-weight).
- *Root stock.*—Not applicable.
- *Own root.*—Yes.
- *Resistance.*—Neither resistance nor susceptibility to diseases or pests has been observed in this variety.

Trunk:

- *Shape.*—Circular.
- *Diameter measured at height of* 15 *cm from soil line.*—Approximately 87 mm.
- *Straps.*—Short.
- *Surface texture.*—Shaggy.
- *Inner bark color.*—Near Dark Grey Orange 165A.
- *Outer bark color.*—Near Dark Greyed-green 197A and Near Grey 201A.

SHOOTS

Young shoot:

- *Form of tip.*—Half open.
- *Distribution of anthocyanin coloration of tip.*—Striped.
- *Intensity of anthocyanin coloration of tip.*—Weak.
- *Density of prostrate hairs on tip.*—Medium.
- *Density of erect hairs on tip.*—Absent.

Woody shoot (mature canes):

- *Shape.*—Slender.
- *Internode length.*—Approximately 54.2 mm.
- *Width at node.*—Approximately 10.8 mm.
- *Cross section.*—Circular.
- *Surface.*—Smooth.
- *Main color.*—Light Brown 164D with Light greyed-yellow 161A.
- *Lenticels.*—Absent.
- *Density of erect hairs on nodes.*—Absent or Very Sparse.
- *Density of erect hairs on internodes.*—Absent or Very Sparse.
- *Growth of auxiliary shoots.*—Medium; Average 17.5 cm/shoot.

Flowering shoot:

- *Vigor during flowering.*—Strong.
- *Attitude during flowering on shoots which are not tied.*—Semi-erect.
- *Color of dorsal side of internodes.*—Green with Red Stripes 144A+187A.
- *Color of ventral side of internodes.*—Green with Red Stripes 144A+187A.
- *Color of dorsal side of nodes.*—Green with Red Stripes 144A+187A.
- *Color of ventral side of nodes.*—Green with Red Stripes 144A+187A.
- *Density of erect hairs on nodes.*—Absent.
- *Erect hairs on internode.*—Absent.
- *Density of prostrate hairs on nodes.*—Absent.
- *Density of prostrate hairs on internodes.*—Absent.
- *Anthocyanin coloration of buds.*—Absent.

Tendrils:

- *Distribution on the shoot at full flowering.*—Discontinuous.
- *Thickness.*—Medium.
- *Color.*—Near Medium Yellow-green 144C.
- *Form.*—Bifurcated.
- *Number of consecutive tendrils.*—Up to 2.
- *Length of tendril.*—Long, approximately 16.6 cm.

LEAVES

Young leaves:

- *Color of upper surface of first* 4 *distal unfolded leaves.*—Green, about 144A.
- *Color of lower surface of first* 4 *distal unfolded leaves.*—Green, about 144A.
- *Average intensity of anthocyanin coloration of six distal leaves prior to flowering.*—Absent.
- *Density of prostrate hairs between veins at lower surface of* 4*th distal unfolded leaf.*—Absent.
- *Density of erect hairs between veins at lower surface of* 4*th distal unfolded leaf.*—Absent.
- *Density of prostrate hairs on veins at lower surface of* 4*th distal unfolded leaf.*—Absent.

*Density of erect hairs on veins at lower surface of 4th distal unfolded leaf.*—Absent.

Mature leaves:

*Average length.*—Approximately 181 mm.
*Average width.*—Approximately 161 mm.
*Size of blade.*—Medium.
*Shape of blade.*—Pentagonal.
*Number of lobes.*—Approximately 5.
*Anthocyanin coloration of main veins on the upper side of the blade.*—Absent.
*Mature leaf profile.*—Flat.
*Blistering surface of blade upper surface.*—Absent.
*Leaf blade tip.*—Flat, in the plane of the leaf.
*Undulation of margin.*—Slight.
*Thickness.*—Medium.
*Undulation of blade between main and lateral veins.*—Absent.
*Shape of teeth.*—Concave on both sides.
*Length of teeth.*—Short.
*Ratio length/width of teeth.*—Small.
*General shape of petiole sinus.*—Slightly open.
*Tooth at petiole sinus.*—Absent.
*Petiole sinus limited by veins.*—Absent.
*Shape of upper lateral sinus.*—Open.
*Depth of upper lateral sinus.*—Very Shallow.
*Density of prostrate hairs between veins on lower surface of blade.*—Absent.
*Density of erect hairs between veins on lower surface of blade.*—Absent.
*Density of prostrate hairs on main veins on lower surface of blade.*—Absent.
*Density of erect hairs on main veins on lower surface of blade.*—Absent.
*Density of prostrate hairs on main veins on upper surface of blade.*—Absent.
*Autumn coloration of leaves.*—Light Yellow-green 153D and Medium Greyed-yellow 162A at December 12.

Upper surface:

*Color.*—Near Dark Green 139A.
*Surface texture.*—Smooth.
*Surface appearance.*—Dull.
*Glossiness.*—Weak.
*Pubescence.*—Absent.

Lower surface:

*Color.*—Medium Green 138A.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:

*Length of petiole.*—Approximately 12 cm.
*Length of petiole compared to middle vein.*—Much shorter.
*Diameter.*—Approximately 4 mm.
*Density of prostrate hairs on petiole.*—Absent.
*Density of erect hairs on petiole.*—Absent.
*Shape of base of petiole sinus.*—U-shaped.
*Color.*—Medium Yellow-green 144C.

Buds:

*Shape.*—Conical.
*Size.*—Medium, approximately 3 mm×4 mm.
*Position.*—Slightly held out, about 60 degrees.
*Cane bud fruitfulness.*—Basal most fruitful.
*Time of bud burst.*—Early, about March 5.

FLOWERS

General:

*Flower sex.*—Hermaphrodite.
*Length of first inflorescence.*—Medium, approximately 18.5 cm.
*Position of first flowering node.*—Fifth node.
*Number of inflorescences per shoot.*—Approximately 1 to 2.
*Date of full bloom.*—Approximately May 20th.
*Time of bloom.*—Medium, about May 10.
*Pollen color.*—Medium greyed-orange, about 167A.
*Petals color.*—Dark green, about 139A.
*Sex of flower.*—Hermaphrodite, fully developed stamens and fully developed gynoecium.
*Size (diameter of fully open flower).*—Medium, approximately 6 mm.

FRUIT

General:

*Ripening period.*—Early, approximately July 1.
*Use.*—Table grapes.
*Keeping quality.*—Good.
*Shipping quality.*—Good.
*Date of first harvest.*—Approximately July 6, 2005.
*Solids-sugar.*—Medium.
*Refractometer test.*—Approximately 17.2%.
*Acid.*—Medium, approximately 0.55 gr./L tartaric acid.
*Juice pH.*—Approximately 3.42.

Cluster:

*Bunch size (peduncle excluded).*—Medium.
*Bunch length (peduncle excluded).*—Medium, approximately 23 cm.
*Bunch width.*—Approximately 19 cm.
*Bunch weight.*—Medium, approximately 350 g.
*Bunch density.*—Medium.
*Number of berries.*—Approximately 99.6.
*Form.*—Cylindrical.

Peduncle:

*Length of peduncle.*—Short, approximately 33 mm.
*Lignification of peduncle.*—Medium.
*Color.*—Near Red-grey 187B.

Berry:

*Size.*—Medium.
*Uniformity of size.*—Uniform.
*Berry weight.*—Medium, approximately 3.6 gr.
*Shape.*—Round.
*Presence of seeds.*—Rudimentary.
*Cross section.*—Circular.
*Dimensions.*—Longitudinal axis: Approximately 18.6 mm. Horizontal axis: Approximately 18.2 mm.
*Skin color (without bloom).*—Red-grey 187B.
*Flesh color.*—Light greyed-yellow about 161A.
*Juiciness of flesh.*—Slightly juicy.
*Berry firmness.*—Firm.
*Particular flavor.*—Muscat.
*Bloom (cuticular wax).*—Weak.
*Pedicel length.*—Long, approximately 8.9 mm.
*Berry separation from pedicel.*—Medium.
*Visibility of hilum.*—Slightly.

Skin:

*Thickness.*—Medium.

*Texture.*—Medium.

*Reticulation.*—Absent.

*Roughness.*—Absent.

*Tenacity.*—Tenacious to flesh.

Seed:

*Number of seeds per berry.*—Approximately 0.46.

*Size.*—Small.

*Color.*—light green.

*Texture.*—Medium.

*Endosperm.*—Absent.

*Fresh weight of seed-traces/berry.*—Approximately 2.35 mg.

*Room-dry weight of seed-traces/berry.*—Approximately 1.52 mg.

What is claimed is:

1. A new and distinct variety of grapevine as herein illustrated and described.

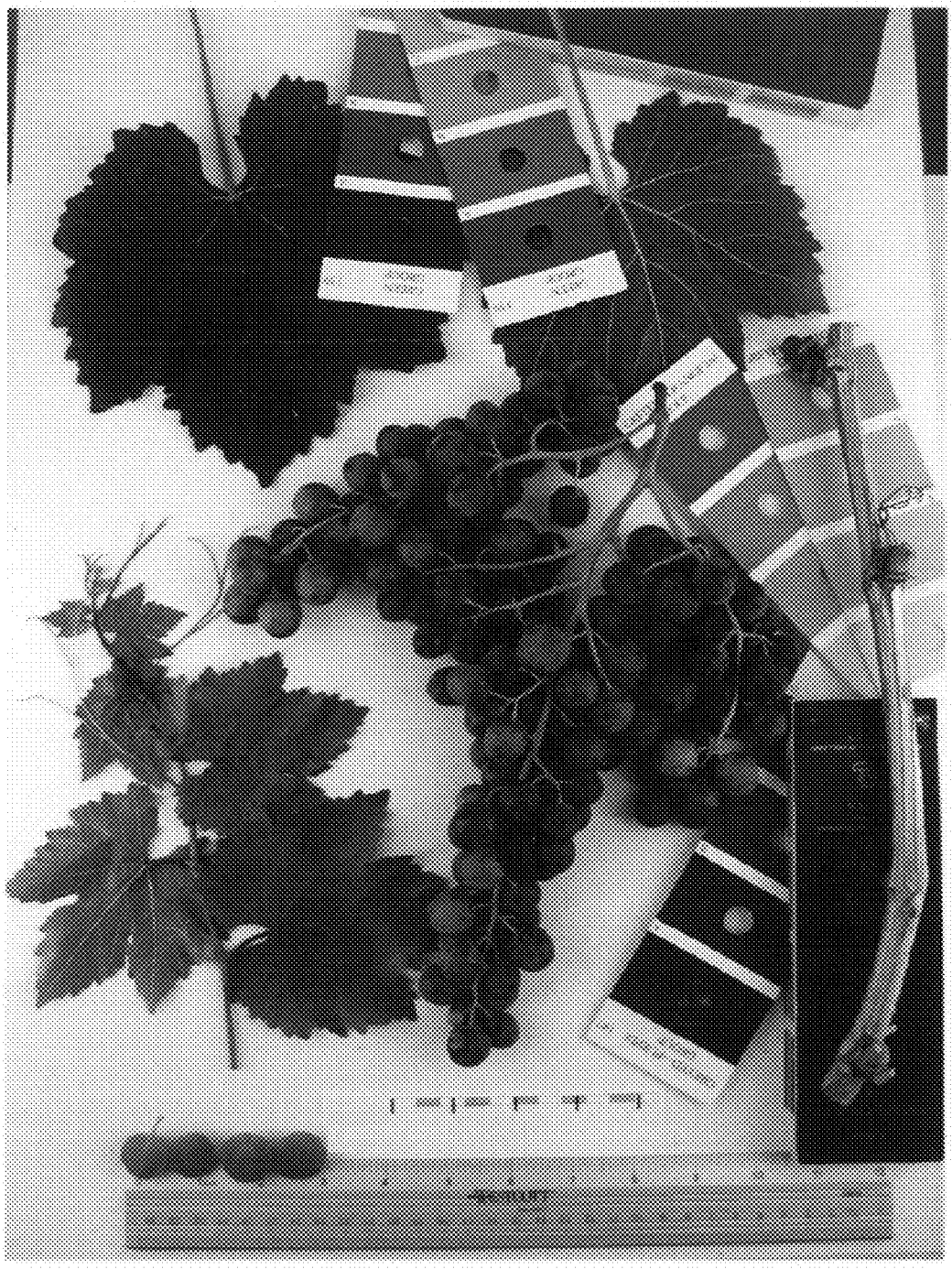

* * * * *